United States Patent
Tadaoka et al.

(10) Patent No.: US 10,519,170 B2
(45) Date of Patent: Dec. 31, 2019

(54) COMPLEX AND PROCESS FOR PREPARING COMPLEX

(71) Applicants: Dunlop Sports Co., Ltd., Kobe-shi, Hyogo (JP); Sumitomo Rubber Industries, Ltd., Kobe-shi, Hyogo (JP)

(72) Inventors: Hiroshi Tadaoka, Kobe (JP); Kazuyoshi Shiga, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 0 days.

(21) Appl. No.: 15/850,905

(22) Filed: Dec. 21, 2017

(65) Prior Publication Data
US 2018/0186816 A1 Jul. 5, 2018

(30) Foreign Application Priority Data
Dec. 22, 2016 (JP) ................ 2016-250051

(51) Int. Cl.
*C07F 3/06* (2006.01)
*C01G 9/02* (2006.01)
(Continued)

(52) U.S. Cl.
CPC .......... *C07F 3/06* (2013.01); *C01G 9/02* (2013.01); *C07C 57/04* (2013.01); *C07C 57/18* (2013.01);
(Continued)

(58) Field of Classification Search
None
See application file for complete search history.

(56) References Cited

FOREIGN PATENT DOCUMENTS

| EP | 0328979 | * | 2/1989 | ............ C08F 230/04 |
| JP | 1-245859 A | | 10/1989 | |

OTHER PUBLICATIONS

Gordon et al., "Preparation and properties of tetrazinc μ4-oxohexa-μ-carboxylates (basic zinc carboxylates)", Canadian Journal of Chemistry, 61, 1983, pp. 1218-1221.
(Continued)

*Primary Examiner* — Clinton A Brooks
(74) *Attorney, Agent, or Firm* — Birch, Stewart, Kolasch & Birch LLP

(57) ABSTRACT

An object of the present invention is to provide a novel complex having at least two carbon-carbon double bonds and/or carbon-carbon triple bonds. The present invention provides a complex represented by a structural formula (2):

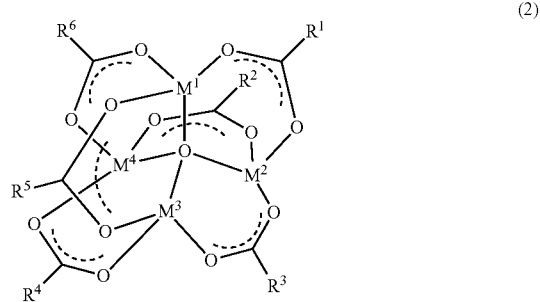

[In the structural formula (2), $M^1$ to $M^4$ are identical to or different from each other and represent a metal atom, $R^1$ to $R^6$ are identical to or different from each other and represent a hydrogen atom, an alkyl group having 1 to 18 carbon atoms, an alkenyl group having 2 to 18 carbon atoms or an
(Continued)

alkynyl group having 2 to 18 carbon atoms, and at least two of $R^1$ to $R^6$ are the alkenyl group having 2 to 18 carbon atoms or the alkynyl group having 2 to 18 carbon atoms.].

10 Claims, 4 Drawing Sheets

(51) Int. Cl.
*C07F 3/00* (2006.01)
*C07C 57/18* (2006.01)
*C07C 57/04* (2006.01)

(52) U.S. Cl.
CPC .......... *C07F 3/003* (2013.01); *C01P 2002/72* (2013.01); *C01P 2002/82* (2013.01); *C01P 2002/87* (2013.01)

(56) References Cited

OTHER PUBLICATIONS

New Experimental Chemical Lecture, Edition 1st, vol. 8th, pp. 986-987.
Ötvös et al., "Synthesis and Spectroscopic and Computational Characterization of Zn4O(Alicyclic or Aromatic Carboxylate)6 Complexes as Potential MOF Precursors", Inorganic Chemistry, 2010, 49, pp. 4620-4625.

\* cited by examiner

COMPLEX AND PROCESS FOR PREPARING COMPLEX

FIELD OF THE INVENTION

The present invention relates to a complex, more specifically, a complex having a reactive functional group. Further, the present invention relates to a process for preparing a complex.

DESCRIPTION OF THE RELATED ART

Japanese Patent Publication No. H1-245859 A discloses a macro porous ion selective exchange resin obtained by a crosslinking polymerization of a well-defined polymerizable metal complex, wherein the macro porous ion selective exchange resin is obtained by reacting a metal complex represented by a general formula of MaLbBcXd (1) with a monomer having at least two polymerizable carbon-carbon multiple bonds and/or an oligomer crosslinking agent (In the formula, M represents a main group metal and/or a sub group metal, L represents a polymerizable ligand, B represents a non-polymerizable ligand, X represents a non-polymerizable anion, a represents an integer of 1 to 6, b represents an integer of 1 to 8, c represents an integer of 0 to 4, and d represents an integer of 0 to 6.).

New Experimental Chemical Lecture, Edition 1$^{st}$, Volume 8$^{th}$, p. 986 discloses a process for preparing tetrazinc monoxide hexaacetate by heating zinc acetate (II) in vacuum.

Inorganic Chem. 2010, 49, 4620-4625 discloses a process for preparing Zn$_4$O carboxylate by reacting a carboxylic acid with zinc oxide in carbon tetrachloride.

Can. J. Chem. 1983, 61, 1218 discloses a process for preparing a basic zinc 2-ethylhexanoate by reacting zinc oxide with zinc 2-ethylhexanoate in toluene.

SUMMARY OF THE INVENTION

An object of the present invention is to provide a novel complex having at least two carbon-carbon double bonds and/or carbon-carbon triple bonds. In addition, if a conventional preparing process is used to prepare the novel complex having at least two carbon-carbon double bonds and/or carbon-carbon triple bonds, there is a problem that the carbon-carbon double bonds and/or the carbon-carbon triple bonds are self-polymerized, thereby failing to obtain the target complex. The present invention has been made in view of the abovementioned circumstances, and an object of the present invention is to provide a novel preparing process for preparing a complex.

The present invention relates to a complex represented by a formula (1):

[In the formula (1), M is a metal atom, and R is a hydrogen atom, an alkyl group having 1 to 18 carbon atoms, an alkenyl group having 2 to 18 carbon atoms or an alkynyl group having 2 to 18 carbon atoms. In the formula (1), a plurality of R may be identical to or different from each other, at least two of R are the alkenyl group having 2 to 18 carbon atoms or the alkynyl group having 1 to 18 carbon atoms, and n is an integer of 1 to 8.].

The complex represented by the formula (1) is preferably a complex represented by a structural formula (2):

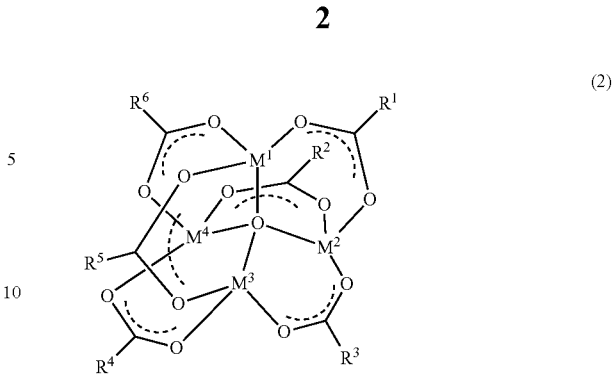

[In the structural formula (2), M$^1$ to M$^4$ are identical to or different from each other and represent a metal atom, R$^1$ to R$^6$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least two of R$^1$ to R$^6$ are the alkenyl group having 2 to 18 carbon atoms or the alkynyl group having 2 to 18 carbon atoms.].

In a preferable complex according to the present invention, M$^1$ to M$^4$ are zinc and R$^1$ to R$^6$ are —CH=CH$_2$ or —C(CH$_3$)=CH$_2$ in the structural formula (2).

The present invention also provides a process for preparing a complex comprising a step of conducting a reaction between a compound represented by a formula (3) and a metal oxide represented by a formula (4) in a solvent:

[In the formula (3), M$^5$ is a metal atom, R is a hydrogen atom, an alkyl group having 1 to 18 carbon atoms, an alkenyl group having 2 to 18 carbon atoms or an alkynyl group having 2 to 18 carbon atoms, x is a number corresponding to oxidation number of the metal atom M$^5$ and is an integer of 2 or more, and a plurality of R may be identical to or different from each other. In the formula (4), M$^6$ is a metal atom, a is an integer of 1 to 5, and b is an integer of 1 to 7.].

Dichloromethane is preferably used as the solvent. A molar ratio ((3)/(4)) of the compound represented by the formula (3) to the metal oxide represented by the formula (4) preferably ranges from 3/2 to 5/1.

The reaction between the compound represented by the formula (3) and the metal oxide represented by the formula (4) is preferably conducted at a temperature in a range from −20° C. to 100° C.

The preparing process according to the present invention is suitable for a process for preparing the complex represented by the formula (1) and the complex represented by the structural formula (2).

According to the present invention, a novel complex having at least two carbon-carbon double bonds and/or carbon-carbon triple bonds is obtained. In addition, a novel preparing process for preparing a complex is provided.

DESCRIPTION OF THE PREFERRED EMBODIMENT

Figure 1:
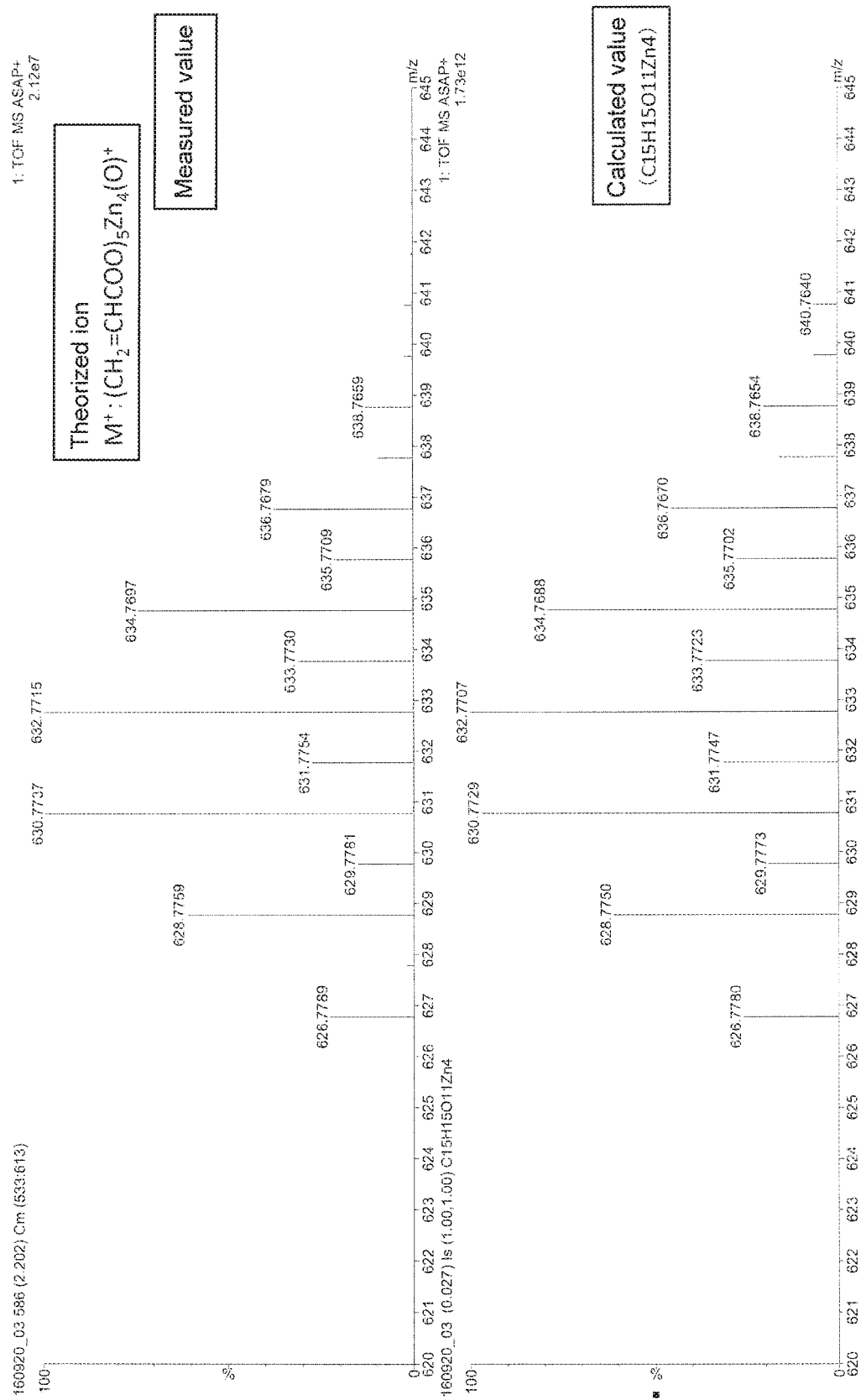
FIG. 1 shows ASAP-MS spectrum of a preferable complex according to the present invention.

The present invention relates to a complex represented by a formula (1):

[M$_4$O(RCOO)$_6$]$_n$     (1)

[In the formula (1), M is a metal atom, O is an oxygen atom, RCOO is a carboxylate group, and R is a hydrogen atom, an alkyl group having 1 to 18 carbon atoms, an alkenyl group having 2 to 18 carbon atoms or an alkynyl group having 2 to 18 carbon atoms. In the formula (1), a plurality of R may be identical to or different from each other, at least two of R are the alkenyl group having 2 to 18 carbon atoms or the alkynyl group having 2 to 18 carbon atoms, and n is an integer of 1 to 8.].

A complex means a molecular compound having a metal atom or metal ion to which an atom or atomic group called a ligand is binding, and is also called a coordination compound.

Examples of the metal atom (M) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. These metal atoms may be used solely, or at least two of them may be used. Among them, as the metal atom, beryllium, magnesium, calcium, zinc, barium, cadmium, lead, copper or nickel is preferable, beryllium, magnesium, calcium, zinc, barium, cadmium or lead is more preferable, and zinc is even more preferable.

The oxidation number of the metal atom (M) is preferably +2.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecylgroup, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms include ethenyl group (vinyl group), 1-propenyl group, 2-propenyl group, isopropenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, and octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable. The position of the carbon-carbon double bond is preferably α, β-position or a terminal of the alkenyl group. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms include ethynyl group, 1-propynyl group, 2-propynyl group, butynyl group, pentynyl group, hexynyl group, heptynyl group, octynyl group, nonynyl group, decynyl group, undecynyl group, dodecynyl group, tridecynyl group, tetradecynyl group, pentadecynyl group, hexadecynyl group, heptadecynyl group, and octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable. The position of the carbon-carbon triple bond is preferably α, β-position or a terminal of the alkynyl group. The alkynyl group preferably has 8 or less carbon atoms, more preferably has 6 or less carbon atoms, and even more preferably has 4 or less carbon atoms. Preferable examples of the alkynyl group having 2 to 18 carbon atoms include ethynyl group, 1-propynyl group and 2-propynyl group.

In the formula (1), at least two of R are the alkenyl group having 2 to 18 carbon atoms or the alkynyl group having 2 to 18 carbon atoms. The complex represented by the formula (1) has two or more carbon-carbon unsaturated bonds. If the complex represented by the formula (1) has two or more carbon-carbon unsaturated bonds, the complex represented by the formula (1) can, for example, have a crosslinking reaction with a monomer having an ethylenically double bond. The number of the alkenyl group having 2 to 18 carbon atoms or alkynyl group having 2 to 18 carbon atoms in R is preferably 3 or more, more preferably 4 or more, even more preferably 5 or more, and most preferably 6.

In the formula (1), at least two of R are preferably an alkenyl group having 2 to 18 carbon atoms and a carbon-carbon double bond at a terminal, or an alkynyl group having 2 to 18 carbon atoms and a carbon-carbon triple bond at a terminal. The number of the alkenyl group having 2 to 18 carbon atoms and a carbon-carbon double bond at a terminal or alkynyl group having 2 to 18 carbon atoms and having a carbon-carbon triple bond at a terminal in R is preferably 3 or more, more preferably 4 or more, even more preferably 5 or more, and most preferably 6.

In the formula (1), six R may be identical to or different from each other, and are preferably all identical to each other.

Examples of the complex represented by the formula (1) include a complex in which all the R are vinyl group and the metal atom (M) is zinc; and a complex in which all the R are isopropenyl group and the metal atom (M) is zinc.

In the complex represented by the formula (1), n may be an integer of 1 or more. In the complex represented by the formula (1), a structure with n=1 is represents a basic structural unit of the complex, and a complex having a structure with an integral multiple of this basic structural unit is included in the present invention. In the present invention, n is preferably an integer of 1 to 8, more preferably an integer of 2 to 8.

Examples of the structure of the complex represented by the formula (1) include a structure having four metal atoms (M) binding to an oxygen atom (O) and a carboxylate group (RCOO) coordinating to the metal atoms. Examples of the configuration of the four metal atoms binding to the oxygen atom include a regular tetrahedron configuration and a planar quadrangle configuration. In addition, the coordination mode of the carboxylate group to the metal atoms is bidentate coordination. It is noted that the two oxygen atoms of the carboxylate group may coordinate to the different metal atom or to the same metal atom, and preferably coordinate to the different metal atom.

In the present invention, the complex represented by the formula (1) is preferably a complex represented by a structural formula (2):

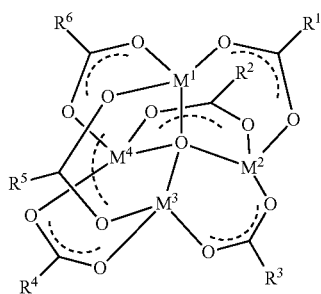
(2)

[In the structural formula (2), $M^1$ to $M^4$ are identical to or different from each other and represent a metal atom, $R^1$ to $R^6$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least two of $R^1$ to $R^6$ are the alkenyl group having 2 to 18 carbon atoms or the alkynyl group having 2 to 18 carbon atoms.].

In the complex represented by the structural formula (2), the oxygen atom exists at a center of a regular tetrahedron configuration, and the metal atoms $M^1$ to $M^4$ locate at four corners of the regular tetrahedron configuration. Such structure is called a tetranucleus metal cluster structure. One oxygen atom in three carboxylate groups each coordinates to the metal atom $M^1$ to $M^4$ constituting one nucleus. Four oxygen atoms binding to the metal atom $M^1$ to $M^4$ locate at four corners of the regular tetrahedron configuration having the metal atom $M^1$ to $M^4$ as the center.

In the structural formula (2), the dotted line shows a resonance hybrid of the carbonyl bond (—C=O) and the single bond (—C—O—) in the carboxylate group. In addition, in the structural formula (2), the covalent bond and the coordination bond are both shown in a solid line.

Examples of the metal atom represented by $M^1$ to $M^4$ in the structural formula (2) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. These metal atoms may be used solely, or at least two of them may be used. Among them, as the metal atom, beryllium, magnesium, calcium, zinc, barium, cadmium, lead, copper or nickel is preferable, beryllium, magnesium, calcium, zinc, barium, cadmium or lead is more preferable, and zinc is even more preferable. The oxidation number of the metal atoms $M^1$ to $M^4$ is preferably +2. The metal atoms $M^1$ to $M^4$ may be different from each other, but are preferably all the same metal atom.

Examples of the alkyl group having 1 to 18 carbon atoms represented by $R^1$ to $R^6$ in the structural formula (2) include methyl group, ethyl group, propyl group, butyl group, pentyl group, hexyl group, heptyl group, octyl group, nonyl group, decyl group, undecyl group, dodecylgroup, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms represented by $R^1$ to $R^6$ in the structural formula (2) include ethenyl group (vinyl group), 1-propenyl group, 2-propenyl group, isopropenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, and octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable. The position of the carbon-carbon double bond is preferably α, β-position or a terminal of the alkenyl group. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms represented by $R^1$ to $R^6$ in the structural formula (2) include ethynyl group, 1-propynyl group, 2-propynyl group, butynyl group, pentynyl group, hexynyl group, heptynyl group, octynyl group, nonynyl group, decynyl group, undecynyl group, dodecynyl group, tridecynyl group, tetradecynyl group, pentadecynyl group, hexadecynyl group, heptadecynyl group, and octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable. The position of the carbon-carbon triple bond is preferably α, β-position or a terminal of the alkynyl group. The alkynyl group preferably has 8 or less carbon atoms, more preferably 6 or less carbon atoms, and even more preferably 4 or less carbon atoms. Preferable examples of the alkynyl group having 2 to 18 carbon atoms include ethynyl group, 1-propynyl group and 2-propynyl group.

In the structural formula (2), at least two of $R^1$ to $R^6$ are the alkenyl group having 2 to 18 carbon atoms or the alkynyl group having 2 to 18 carbon atoms. The number of the alkenyl group having 2 to 18 carbon atoms or alkynyl group having 2 to 18 carbon atoms in $R^1$ to $R^6$ is preferably 3 or more, more preferably 4 or more, even more preferably 5 or more, and most preferably 6.

In the structural formula (2), at least two of $R^1$ to $R^6$ are preferably an alkenyl group having 2 to 18 carbon atoms and a carbon-carbon double bond at a terminal, or an alkynyl group having 2 to 18 carbon atoms and a carbon-carbon triple bond at a terminal. The number of the alkenyl group having 2 to 18 carbon atoms and a carbon-carbon double bond at a terminal or alkynyl group having 2 to 18 carbon atoms and a carbon-carbon triple bond at a terminal in $R^1$ to $R^6$ is preferably 3 or more, more preferably 4 or more, even more preferably 5 or more, and most preferably 6.

In the structural formula (2), $R^1$ to $R^6$ may be identical to or different from each other, and are preferably all identical to each other.

Examples of the complex having the structural formula (2) include a complex (zinc acrylate oxo cluster) in which all the $R^1$ to $R^6$ are vinyl group (—CH═CH$_2$) and the metal atoms ($M_1$ to $M_4$) are zinc; and a complex (zinc methacrylate oxo cluster) in which all the $R^1$ to $R^6$ are isopropenyl group (—C(CH$_3$)═CH$_2$) and the metal atoms ($M_1$ to $M_4$) are zinc.

The complex represented by the formula (1) and the complex having the structural formula (2) according to the present invention are instable to water. Thus, the amount of water in the complex is preferably controlled to 250 ppm or less, more preferably 100 ppm or less, and even more preferably 50 ppm or less. In addition, when the complex is stored, the complex is preferably stored in an environment with a relative humidity of 30% or less, more preferably 20% or less, and even more preferably 10% or less.

The present invention further includes a process for preparing a complex, comprising a step of conducting a reaction between a compound represented by a formula (3) and a metal oxide represented by a formula (4) in a solvent:

  (3)

  (4)

[In the formula (3), $M^5$ is a metal atom, R is a hydrogen atom, an alkyl group having 1 to 18 carbon atoms, an alkenyl group having 2 to 18 carbon atoms or an alkynyl group having 2 to 18 carbon atoms, x is a number corresponding to oxidation number of the metal atom $M^5$ and is an integer of 2 or more, y is an integer of 0 or more, and a plurality of R may be identical to or different from each other. In the formula (4), $M^6$ is a metal atom, a is an integer of 1 to 5, and b is an integer of 1 to 7.].

It is noted that, in the description of the present invention, the compound represented by the formula (3) is sometimes simply referred to as "compound (3)", and the metal oxide represented by the formula (4) is sometimes simply referred to as "metal oxide (4)".

The materials used in the process for preparing the complex according to the present invention will be explained. R in the compound (3) is a hydrogen atom, an alkyl group having 1 to 18 carbon atoms, an alkenyl group having 2 to 18 carbon atoms, or an alkynyl group having 2 to 18 carbon atoms.

Examples of the alkyl group having 1 to 18 carbon atoms include methyl group, ethyl group, propyl group, butyl group, pentyl group, hexyl group, heptyl group, octyl group, nonyl group, decyl group, undecyl group, dodecylgroup, tridecyl group, tetradecyl group, pentadecyl group, hexadecyl group, heptadecyl group, and octadecyl group. The alkyl group having 1 to 18 carbon atoms may have a linear structure, a branched structure or a cyclic structure, and the linear structure is preferable.

Examples of the alkenyl group having 2 to 18 carbon atoms include ethenyl group (vinyl group), 1-propenyl group, 2-propenyl group, isopropenyl group, butenyl group, pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, and octadecenyl group. The alkenyl group having 2 to 18 carbon atoms may have a linear structure or a branched structure, and the linear structure is preferable. As the alkenyl group having 2 to 18 carbon atoms, an alkenyl group having one carbon-carbon double bond is preferable. The position of the carbon-carbon double bond is preferable α, β-position or a terminal of the alkenyl group. The alkenyl group preferably has 8 or less carbon atoms, more preferably 6 or less carbon atoms, and even more preferably 4 or less carbon atoms. Preferable examples of the alkenyl group having 2 to 18 carbon atoms include vinyl group, isopropenyl group, 1-propenyl group and 2-propenyl group.

Examples of the alkynyl group having 2 to 18 carbon atoms include ethynyl group, 1-propynyl group, 2-propynyl group, butynyl group, pentynyl group, hexynyl group, heptynyl group, octynyl group, nonynyl group, decynyl group, undecynyl group, dodecynyl group, tridecynyl group, tetradecynyl group, pentadecynyl group, hexadecynyl group, heptadecynyl group, and octadecynyl group. The alkynyl group having 2 to 18 carbon atoms may have a linear structure or a branched structure, and the linear structure is preferable. As the alkynyl group having 2 to 18 carbon atoms, an alkynyl group having one carbon-carbon triple bond is preferable. The position of the carbon-carbon triple bond is preferable α, β-position or a terminal of the alkynyl group. The alkynyl group preferably has 8 or less carbon atoms, more preferably 6 or less carbon atoms, and even more preferably 4 or less carbon atoms. Preferable examples of the alkynyl group having 2 to 18 carbon atoms include ethynyl group, 1-propynyl group and 2-propynyl group.

Examples of the metal atom ($M^5$) in the formula (3) include an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; and a base metal such as beryllium, magnesium, aluminum, zinc, gallium, cadmium, indium, tin, thallium, lead, bismuth and polonium. Among them, as the metal atom, the metal atom capable of forming a divalent metal ion is preferable, beryllium, magnesium, calcium, zinc, barium, cadmium or lead is more preferable. These metal atoms may be used solely, or a mixture of at least two of them may be used.

x represents a number of the carboxylate groups (RCOO) in the compound (3). x is a number corresponding to oxidation number of the metal atom $M^5$, and is an integer of 2 or more. x is, for example, preferably 2 to 5, more preferably 2. y is an integer of 0 or more, and is, for example, preferably 0 to 5, more preferably 0. This is because if y is 1 or more, the yield of the target complex tends to be lowered.

Preferable specific examples of the compound (3) include a fatty acid metal salt with y=0 in the formula (3). Examples of the fatty acid constituting the fatty acid metal salt include a saturated fatty acid having 1 to 19 carbon atoms, and an unsaturated fatty acid having 3 to 20 carbon atoms.

Examples of the saturated fatty acid include methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and nonadecanoic acid. Examples of the unsaturated fatty acid include an unsaturated fatty acid having a carbon-carbon double bond such as propenoic acid (acrylic acid), 2-methylprop-2-enoic acid (methacrylic acid), 2-butenoic acid, 3-butenoic acid, 4-pentenoic acid, 5-hexenoic acid, 6-heptenoic acid, 7-octenoic acid, 8-nonenoic acid, 9-decenoic acid, 10-undecenoic acid, 11-dodecenoic acid, 12-tridecenoic acid, 9-tetradecenoic acid, 13-tetradecenoic acid, 14-pentadecenoic acid, 9-hexadecenoic acid, 15-hexadecenoic acid, 16-heptadecenoic acid, 9-octadecenoic acid, 11-octadecenoic acid, 17-octadecenoic acid and 18-nonadecenoic acid; and an unsaturated fatty acid having a carbon-carbon triple bond such as propiolic acid, 3-butynoic acid, 4-pentynoic acid, 5-hexynoic acid, 6-heptynoic acid, 7-octynoic acid, 8-nonynoic acid, 9-decynoic acid, 10-undecynoic acid, 11-dodecynoic acid, 12-tridecynoic acid, 9-tetradecynoic acid, 13-tetradecynoic acid, 14-pentadecynoic acid, 9-hexadecynoic acid, 15-hexadecynoic acid, 16-heptadecynoic acid, 9-octadecynoic acid, 11-octadecynoic acid, 17-octadecynoic acid, and 18-nonadecynoic acid.

As the unsaturated fatty acid having a carbon-carbon double bond, a fatty acid having one carbon-carbon double bond is preferable. The position of the carbon-carbon double bond is preferably α, β-position or a terminal of the unsaturated fatty acid. As the unsaturated fatty acid having a carbon-carbon triple bond, a fatty acid having one carbon-carbon triple bond is preferable. The position of the carbon-carbon triple bond is preferable α, β-position or a terminal of the unsaturated fatty acid.

Examples of the metal atom ($M^5$) of the fatty acid metal salt include an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; a base metal such as beryllium, magnesium, aluminum, zinc, gallium, cadmium, indium, tin, thallium, lead, bismuth and polonium. Among them, as the metal atom, the metal atom capable of forming a divalent metal ion is preferable, and beryllium, magnesium, calcium, zinc, barium, cadmium or lead is more preferable. These metal ions may be used solely, or a mixture of at least two of them may be used.

As the fatty acid metal salt, the fatty acid metal salt in which the metal ion is a divalent metal ion is preferable, the unsaturated fatty acid metal salt in which the metal ion is a divalent metal ion is more preferable, the acrylic acid or methacrylic acid metal salt in which the metal ion is a divalent metal ion is even more preferable, and zinc acrylate or zinc methacrylate is most preferable.

When two or more of the fatty acid metal salts are used in combination as the compound (3), the amount of each fatty acid metal salt can be appropriately adjusted in accordance with the desirable complex. The amount of the unsaturated fatty acid in the fatty acid constituting the fatty acid metal salt is preferably 33 mol % or more, more preferably 50 mol % or more, and even more preferably 66 mol % or more. It is also preferable that all the fatty acids constituting the fatty acid metal salt are the unsaturated fatty acid. In addition, the amount of the unsaturated fatty acid having a carbon-carbon double bond in the fatty acid constituting the fatty acid metal salt is preferably 33 mol % or more, more preferably 50 mol % or more, and even more preferably 66 mol % or more. It is also preferable that all the fatty acids constituting the fatty acid metal salt are the unsaturated fatty acid having a carbon-carbon double bond. As the fatty acid constituting the fatty acid metal salt, a plurality of fatty acids may be used in combination, but one fatty acid is preferably used.

Examples of the embodiment of the fatty acid metal salt include an embodiment including one fatty acid and one metal ion; an embodiment including a plurality of fatty acids and one metal ion; an embodiment including one fatty acid and a plurality of metal ions; and an embodiment including a plurality of fatty acids and a plurality of metal ions. Among them, the embodiment including one fatty acid and one metal ion is preferable.

The above fatty acid metal salt may be used solely, or at least two of them may be used in combination.

In the present invention, zinc acrylate and/or zinc methacrylate is preferably used as the compound (3).

In the preparing process according to the present invention, the metal oxide represented by the formula (4) is used.

$$M^6{}_aO_b \quad (4)$$

Examples of the metal atom ($M^6$) include an alkali metal such as lithium, sodium, potassium, rubidium and cesium; an alkaline earth metal such as calcium, strontium and barium; a transition metal such as scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold; a base metal such as beryllium, magnesium, aluminum, zinc, gallium, cadmium, indium, tin, thallium, lead, bismuth and polonium. Among them, as the metal atom $M^6$, the metal atom capable of forming a divalent metal ion is preferable, and beryllium, magnesium, calcium, zinc, barium, cadmium or lead is more preferable. These metal atoms may be used solely, or a mixture of at least two of them may be used.

In the preparing process according to the present invention, the metal atom $M^5$ in the compound (3) and the metal atom $M^6$ in the metal oxide (4) may be identical to or different from each other, and are preferably identical to each other.

In the metal oxide (4), a is preferably an integer of 1 or more and 5 or less, more preferably an integer of 1 or more and 3 or less, and most preferably 1, and b is preferably an integer of 1 or more and 7 or less, more preferably an integer of 1 or more and 5 or less, even more preferably an integer of 1 or more and 3 or less, and most preferably 1. As the metal oxide (4), a divalent metal oxide with a=1 and b=1 is preferable.

Specific examples of the metal oxide (4) include an alkali metal oxide such as lithium oxide, sodium oxide, potassium oxide, rubidium oxide and cesium oxide; an alkaline earth metal oxide such as calcium oxide, strontium oxide and barium oxide; a transition metal oxide such as scandium oxide, titanium oxide, vanadium oxide, chromium oxide, manganese oxide, iron oxide, cobalt oxide, nickel oxide, copper oxide, yttrium oxide, zirconium oxide, niobium oxide, molybdenum oxide, technetium oxide, ruthenium oxide, rhodium oxide, palladium oxide, silver oxide, hafnium oxide, tantalum oxide, tungsten oxide, rhenium oxide, osmium oxide, iridium oxide, platinum oxide and gold oxide; and a base metal oxide such as beryllium oxide, magnesium oxide, aluminum oxide, zinc oxide, gallium oxide, cadmium oxide, indium oxide, tin oxide, thallium oxide, lead oxide, bismuth oxide and polonium oxide. These metal oxides may be used solely, or a mixture of at least two of them may be used. Among them, as the metal oxide, the divalent metal oxide is preferable, and beryllium oxide, magnesium oxide, calcium oxide, zinc oxide, barium oxide, cadmium oxide or lead oxide is more preferable. In the present invention, as the metal oxide (4), zinc oxide is most preferably used.

Examples of the solvent used to conduct the reaction in the preparing process according to the present invention include, but are not limited to, dichloromethane, 1,2-dichloroethane, chloroform, chlorobenzene, dichlorobenzene, benzene, toluene, xylene, tetrahydrofuran, 1,4-dioxane, ethyl acetate, propyl acetate, isopropyl acetate, and acetonitrile. From the viewpoint of enhancing the yield of the complex, dichloromethane is preferably used as the solvent.

Specific examples of the process for preparing a complex comprising a step of conducting the reaction between the compound (3) and the metal oxide (4) include a preparing process comprising: a step of dissolving or dispersing the compound (3) and the metal oxide (4) in a first solvent and stirring the resultant reaction liquid (reaction step); a step of removing an insoluble substance from the reaction liquid (insoluble substance removal step); and a step of removing the solvent from the reaction liquid (drying step).

(Reaction Step)

In the reaction step, the compound (3) and the metal oxide (4) are dissolved or dispersed in a first solvent, and the resultant reaction liquid is stirred. In this step, the compound (3) and the metal oxide (4) are allowed to contact each other in the solvent to produce the complex.

Specifically, firstly, the metal oxide (4) is dissolved or dispersed in a solvent in a reaction vessel. While stirring the liquid having the metal oxide (4) dissolved or dispersed in the solvent, a liquid having the compound (3) dissolved or dispersed in a solvent is added therein. The liquid having the compound (3) dissolved or dispersed in the solvent may be added dropwise therein. In this case, the dropwise addition time is preferably, but not limited to, 0.5 hour to 3 hours. The reaction is preferably conducted while further stirring the reaction liquid after the dropwise addition.

The reaction is preferably conducted in an inert gas atmosphere such as nitrogen and argon. In particular, the reaction system is preferably a closed system or a system under an inert gas flow since the produced complex is instable to water.

In the reaction between the compound (3) and the metal oxide (4), the molar ratio ((3)/(4)) of the compound (3) to the metal oxide (4) is preferably 3/2 or more, more preferably 2/1 or more, and is preferably 5/1 or less, more preferably 4/1 or less. This is because if the molar ratio ((3)/(4)) of the compound (3) to the metal oxide (4) falls within the above range, the yield of the obtained complex is higher.

In addition, the amount of the solvent in the reaction is preferably 1000 parts by mass or more, more preferably 2000 parts by mass or more, and even more preferably 3000 parts by mass or more, and is preferably 10000 parts by mass or less, more preferably 8000 parts by mass or less, and even more preferably 6000 parts by mass or less, with respect to 100 parts by mass of a total amount of the compound (3) and the metal oxide (4). If the amount of the solvent is 1000 parts by mass or more, the yield of the complex is higher, and if the amount of the solvent is 10000 parts by mass or less, the synthetic workload can be lowered.

The reaction temperature (temperature of the reaction liquid) is preferably −20° C. or more, more preferably 0° C. or more, even more preferably 10° C. or more, and most preferably 20° C. or more, and is preferably 100° C. or less, more preferably 90° C. or less, even more preferably 80° C. or less, and most preferably 50° C. or less. If the reaction temperature is −20° C. or more, the reaction speed between the compound (3) and the metal oxide (4) can be enhanced. In addition, if the reaction temperature is 100° C. or less, the self-polymerization of the compound (3) can be prevented.

The reaction time is preferably 1 hour or more, more preferably 3 hours or more, and even more preferably 12 hours or more. This is because if the reaction time is too short, the yield of the complex may be lowered. In addition, from the viewpoint of enhancing the productivity, the reaction time is preferably 300 hours or less, more preferably 200 hours or less, and even more preferably 100 hours or less. It is noted that the end of the reaction can be confirmed, for example, by a method of measuring the infrared absorption of a sample taken from the reaction liquid, or by a method of measuring the change in the weight or the like of the component dissolved in the reaction liquid.

(Insoluble Substance Removal Step)

After the reaction, the insoluble substance is removed from the reaction liquid. Examples of the insoluble substance include unreacted raw materials, and the self-polymerized polymer of the compound (3). Examples of the method of removing the insoluble substance include, but are not limited to, a method of filtering the reaction liquid.

(Drying Step)

In the drying step, the solvent is removed from the reaction liquid from which the insoluble substance has been removed. A mixture containing the compound (3) and the produced complex is obtained by removing the solvent.

Examples of the method of removing the solvent include a method of drying under reduced pressure and a method of drying under heating, and the drying under reduced pressure is preferable. When performing the drying under reduced pressure, the reaction liquid may be heated. The temperature of the reaction liquid when performing the drying is preferably 100° C. or less, more preferably 80° C. or less, and even more preferably 60° C. or less.

The preparing process according to the present invention may further comprise a step of purifying the obtained complex. It is noted that when the step of purifying the complex is comprised, the above-mentioned insoluble substance removal step and/or drying step may be omitted. Examples of the purification method include a method of removing the compound (3) from the reaction liquid in the preparing process (a method including a purification step); and a method of performing reprecipitation of the mixture of the complex and the compound (3) obtained in the preparing process (a method including a reprecipitation step). Among them, the method of removing the compound (3) from the reaction liquid in the preparing process is preferable.

(Purification Step)

In the purification step, a second solvent is charged into the reaction liquid from which the insoluble substance has been removed in the preparing process, and the resultant precipitate is removed. Raw materials, by-products and the like dissolved in the first solvent are precipitated by charging the second solvent into the reaction liquid. The purity of the finally obtained complex can be enhanced by removing the precipitate.

The second solvent is not particularly limited, as long as it can selectively precipitate the compound (3) in the reaction liquid. In other words, the solubility of the target complex in the second solvent is higher than the solubility of the compound (3) in the second solvent. Examples of the second solvent include hydrocarbons such as hexane, pentane, cyclohexane and heptane.

The amount of the second solvent may be appropriately adjusted such that the compound (3) can be precipitated. The amount of the second solvent is preferably 10 parts by mass or more, more preferably 20 parts by mass or more, and even more preferably 30 parts by mass or more, and is preferably 200 parts by mass or less, more preferably 150 parts by mass or less, and even more preferably 100 parts by mass or less, with respect to 100 parts by mass of the amount of the first solvent.

In addition, after the second solvent is charged, a part of the first solvent and second solvent may be removed to precipitate the compound (3). As the method of removing a part of the first solvent and second solvent, concentration under reduced pressure is preferable. When performing the concentration under reduced pressure, the reaction liquid may be heated. The temperature of concentrating the reaction liquid is preferably 100° C. or less, more preferably 80° C. or less, and even more preferably 60° C. or less.

Examples of the method of removing the precipitated compound (3) include a method of filtering the reaction liquid. The target complex is obtained by removing the first solvent and the second solvent in the drying step from the reaction liquid from which the precipitate has been removed. It is noted that the purification step may be performed several times depending on the desired purity of the complex.

(Reprecipitation Step)

In the reprecipitation step, the reprecipitation of the mixture of the complex and the compound (3) obtained in the preparing process is performed. Specifically, the mixture of the complex and the compound (3) obtained in the preparing process is dissolved in the first solvent, the second solvent is charged into the resultant solution to precipitate the compound (3), and the precipitate is removed.

As the first solvent and the second solvent used in the reprecipitation step, those listed in the reaction step and the purification step may be used. In addition, the preferable amount of the second solvent and the preferable method of removing the precipitate are identical to those in the purification step. The target complex is obtained by removing the solvent after the precipitate is removed. The preferable method of removing the solvent is identical to that in the drying step. It is noted that the reprecipitation step may be performed several times depending on the desired purity of the target complex.

The preparing process according to the present invention is suitable for a method of preparing the complex represented by the general formula (1) and the complex represented by the structural formula (2). Details of the complex represented by the general formula (1) are as described above, and its gist is as follows.

$[M_4O(RCOO)_6]_n$           (1)

[In the formula (1), M is a metal atom, and R is a hydrogen atom, an alkyl group having 1 to 18 carbon atoms, an alkenyl group having 2 to 18 carbon atoms or an alkynyl group having 2 to 18 carbon atoms. In the formula (1), a plurality of R may be identical to or different from each other, at least two of R are the alkenyl group having 2 to 18 carbon atoms or the alkynyl group having 2 to 18 carbon atoms, and n is an integer of 1 to 8.]

Details of the complex represented by the structural formula (2) are as described above, and its gist is as follows.

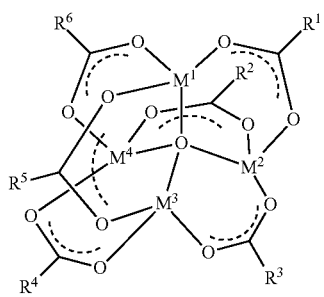

(2)

[In the structural formula (2), $M^1$ to $M^4$ are identical to or different from each other and represent a metal atom, $R^1$ to $R^6$ are identical to or different from each other and represent a hydrogen atom, an alkyl group having 1 to 18 carbon atoms, an alkenyl group having 2 to 18 carbon atoms or an alkynyl group having 2 to 18 carbon atoms, and at least two of $R^1$ to $R^6$ are the alkenyl group having 2 to 18 carbon atoms or the alkynyl group having 2 to 18 carbon atoms.]

EXAMPLES

Next, the present invention will be described in detail by way of examples. However, the present invention is not limited to the examples described below. Various changes and modifications without departing from the spirit of the present invention are included in the scope of the present invention.

[Evaluation Methods]

(1) Direct Introduction-Mass Analysis (DI-MS)

The mass analysis was carried out with a mass analyzer (SynaptG2-S type available from Waters Corporation).

Ionization method: atmospheric solids analysis probe (ASAP)

Measuring mode: Pos., Neg.

Measuring range: m/z=50 to 1500

(2) CHN Element Analysis

The element analysis was carried out with an organic trace element analyzer (Micro Corder JM10 type available from J-Science Lab Co., Ltd.).

(3) Zinc Amount Measurement

The produced complex (0.1171 g) was weighed and put into a beaker with a volume of 100 ml, and 50 ml of distilled water was added to dissolve the complex. Into the resultant liquid, 10 ml of acetic acid-sodium acetate (pH 5) buffer was added, and some drops of a XO indicator (0.1 w/v % of xylenol orange solution for titration available from Wako Pure Chemical Industries, Ltd.: 0.1 g/100 ml=0.001396 M) were added. Finally, distilled water was added to adjust the liquid volume to 100 ml. The obtained liquid was titrated with 0.05 mol/l of an EDTA standard titrant (available from Dojin Chemical, Inc.).

(4) Infrared Spectroscopic Analysis

The infrared spectroscopic analysis was carried out with a Fourier transform infrared spectrophotometer ("measuring instrument: Spectrum One" available from PerkinElmer, Inc.) by a total reflection absorption measuring method (ATR method) using diamond as a prism of the total reflection absorption measurement.

(5) Powder X-Ray Diffraction

The X-ray diffraction measurement was carried out with a wide angle X-ray diffraction instrument ("RINT-TTR III type" available from Rigaku Corporation). The measuring sample was pulverized with an agate mortar. The measuring conditions were as follows.

X-ray source: CuKα X-ray

Tube voltage-tube current: 50 kV-300 mA

Step width: 0.02 deg.

Measuring speed: 5 deg./min

Slit system: light diffusion-light reception-light scattering: 0.5 deg.-opening-0.5 deg.

Monochromator: diffraction curve bent-crystal monochromator

PREPARING EXAMPLES

Inventive Preparing Example 1

Zinc oxide (2.5 g, 31 mmol), zinc acrylate (19.1 g, 92 mmol) and 375 ml of dichloromethane were charged into a reaction vessel, and stirred at 40° C. for 3 hours. It is noted that the solvent was refluxed. The reaction was stopped in three hours after the stirring was started. The obtained reaction liquid was filtered to remove the insoluble precipitate in the solvent. 300 ml of hexane was added into the filtrate, and concentration under reduced pressure was performed until the liquid amount was reduced to about one-fourth, to obtain a precipitate. The precipitate was removed by filtration, and the filtrate was concentrated and dried to obtain a product 1 (5.54 g, yield 26%). Zinc oxide used above was commercially available from Kishida Chemical Co. Ltd., and zinc acrylate used above was commercially available from Sigma-Aldrichi Corporation.

Inventive Preparing Example 2

Under an argon atmosphere, zinc oxide (125 g, 1540 mmol), zinc acrylate (955 g, 4600 mmol) and 18.7 L of dichloromethane were charged into a reaction vessel, and stirred at 40° C. for 3 hours. It is noted that the solvent was refluxed. The obtained reaction liquid was filtered to remove the insoluble precipitate in the solvent. 14.3 L of hexane was added into the filtrate, and concentration under reduced pressure was performed until the liquid amount was reduced to about one-fourth, to obtain a precipitate. The precipitate was removed by filtration, and the filtrate was concentrated and dried to obtain a product 2 (87.4 g, yield 8%).

Inventive Preparing Example 3

The reaction was conducted by the same method as the inventive preparing example 2 except that the reaction time was for 12 hours, to obtain a product 3 (306 g, yield 28%).

Inventive Preparing Example 4

The reaction was conducted by the same method as the inventive preparing example 2 except that the reaction time was 24 hours, to obtain a product 4 (588 g, yield 54%).

Inventive Preparing Example 5

The reaction was conducted by the same method as the inventive preparing example 2 except that the reaction time was 48 hours, to obtain a product 5 (615 g, yield 57%).

The preparing conditions and results of the inventive preparing examples 1 to 5 are summarized in Table 1.

The mass analysis, element analysis, zinc amount measurement, X-ray diffraction measurement and infrared spectroscopic analysis were conducted for the obtained product 5. The experimental results are each shown below.

High-resolution ASAP-MS (positive) spectrum measurement results

Positive ion HR-ASAP-MS m/z: 632.7715

$[M-CH_2CHCOO]^+$ (calcd. For $C_{15}H_{15}O_{11}Zn_4$ 632.7707 Δ1.2 ppm

High-resolution ASAP-MS (negative) spectrum measurement results

Negative ion HR-ASAP-MS m/z: 735.7762

$[M+O_2]^-$ (calcd. For $C_{18}H_{18}O_{15}Zn_4$ 735.7740 Δ2.9 ppm

Anal. Calcd for $C_{18}H_{18}O_{13}Zn_4$: C, 30.71; H, 2.58. Found: C, 30.72; H, 2.50.

Figure 2:
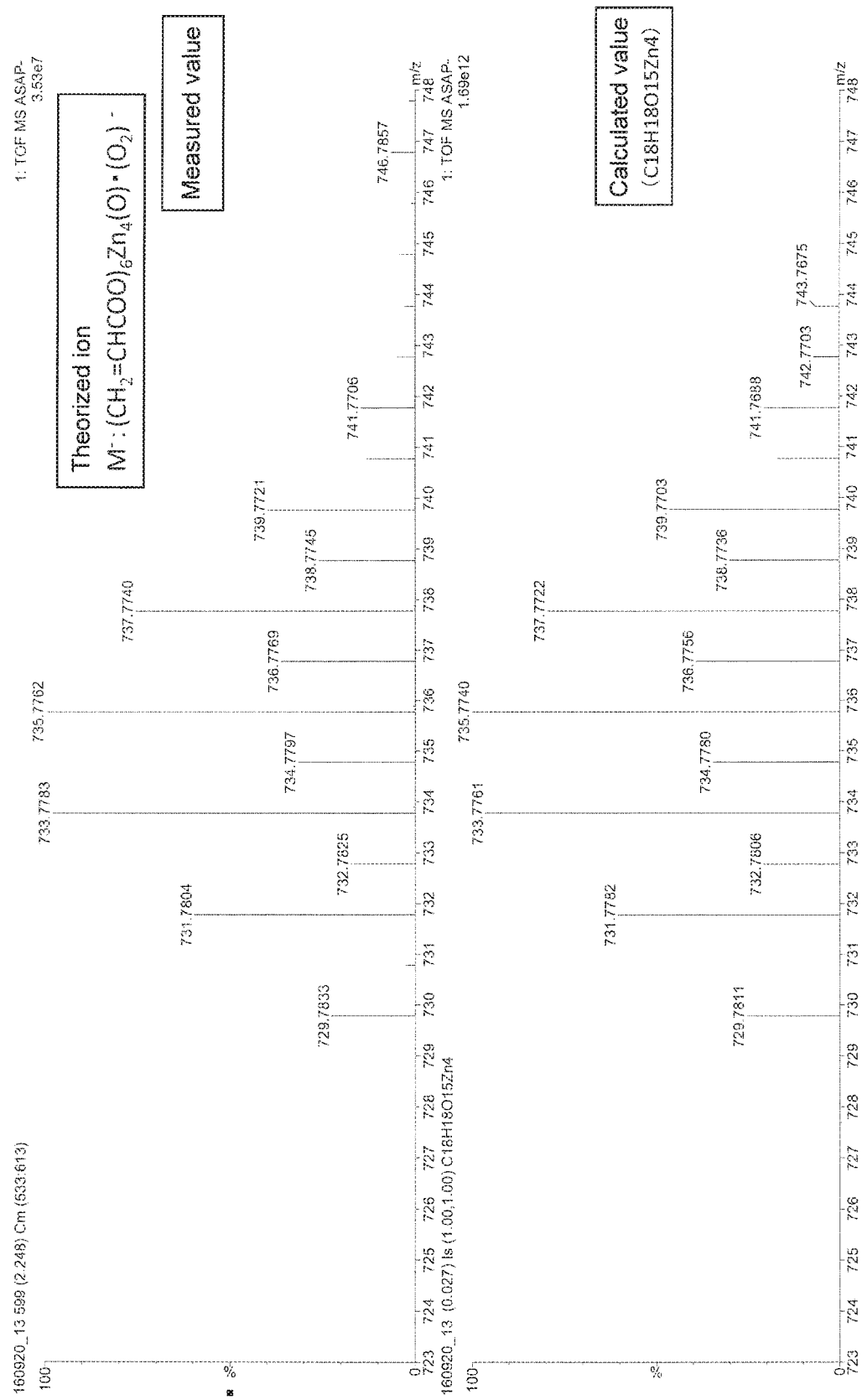
FIG. 2 shows ASAP-MS spectrum of a preferable complex according to the present invention.

IR spectrum peak: 520 $cm^{-1}$, 600 $cm^{-1}$, 675 $cm^{-1}$, 828 $cm^{-1}$, 968 $cm^{-1}$, 1067 $cm^{-1}$, 1276 $cm^{-1}$, 1370 $cm^{-1}$, 1436 $cm^{-1}$, 1572 $cm^{-1}$, 1643 $cm^{-1}$ ASAP-MS spectra of the product 5 are shown in FIGS. 1, 2. In addition, ASAP-MS spectrum simulation patterns of anion $[Zn_4O(OCOCHCH_3)_6O_2]^{(-)}$ and cation $[Zn_4O(OCOCHCH_3)_5](+)$ theorized from $Zn_4O(OCOCHCH_2)_6$ are shown in FIGS. 1, 2. As shown in FIGS. 1, 2, the ASAP-MS spectrum has the same pattern as the simulation pattern. Further, the obtained experimental values 632.7715 and 735.7762 are very close to the estimated values which is 632.7707 for the cation $[Zn_4O(OCOCHCH_3)_5]^{(+)}$: $C_{15}H_{15}O_{11}Zn_4$ and 735.7740 for the anion $[Zn_4O(OCOCHCH_3)_6O_2]^{(-)}$: $C_{18}H_{18}O_{15}Zn_4$. In addition, the measured value of the zinc amount is 36.8 mass %, which is very close to the theoretical value 37.2 mass %. Based on these results, it can be confirmed that the above prepared product 5 is the compound represented by $Zn_4O(OCOCHCH_2)_6$.

The element analysis results show that the product 5 contains carbon in an amount of 30.72 mass % and hydrogen in an amount of 2.50 mass %. The differences between the analysis results and the estimated values were 0.01 mass % for the carbon amount and 0.08 mass % for the hydrogen amount. Since the atomic compositions are very close to the estimated values, it can be confirmed that the product $(Zn_4O(OCOCHCH_2)_6)$ has a very high purity.

Figure 3:
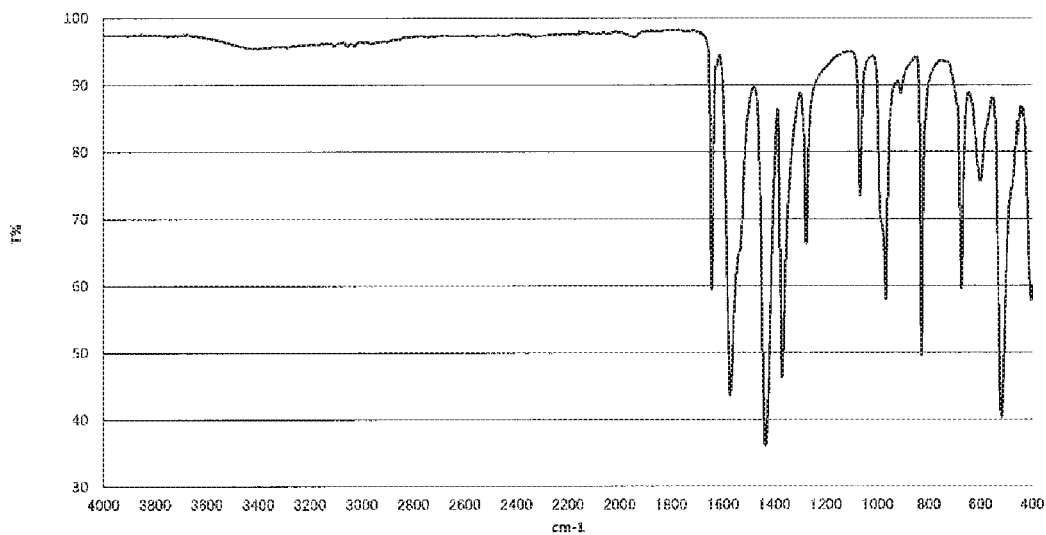
FIG. 3 shows IR spectrum of a preferable complex according to the present invention.
Figure 4:
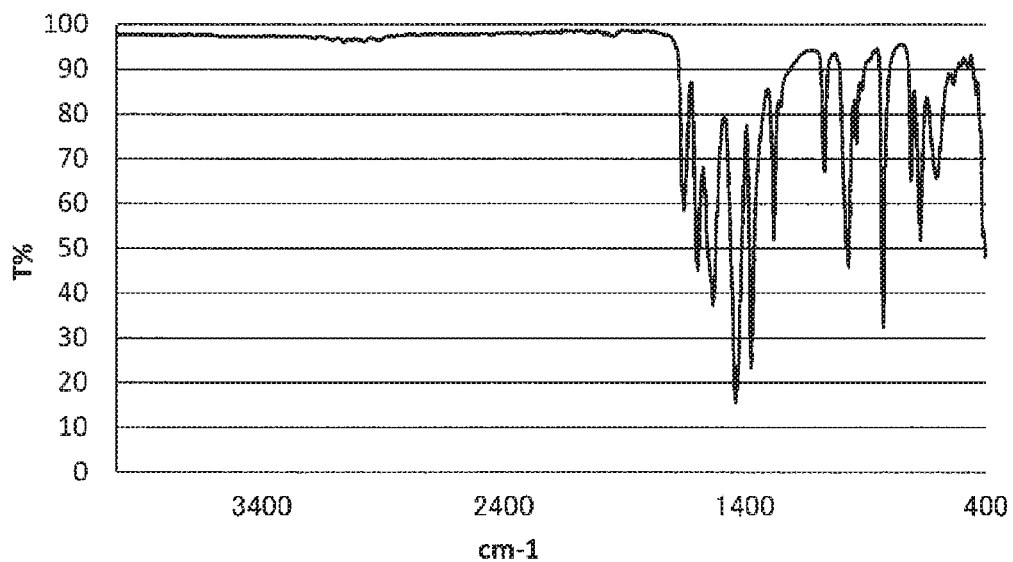
FIG. 4 shows IR spectrum of zinc acrylate.
Figure 5:
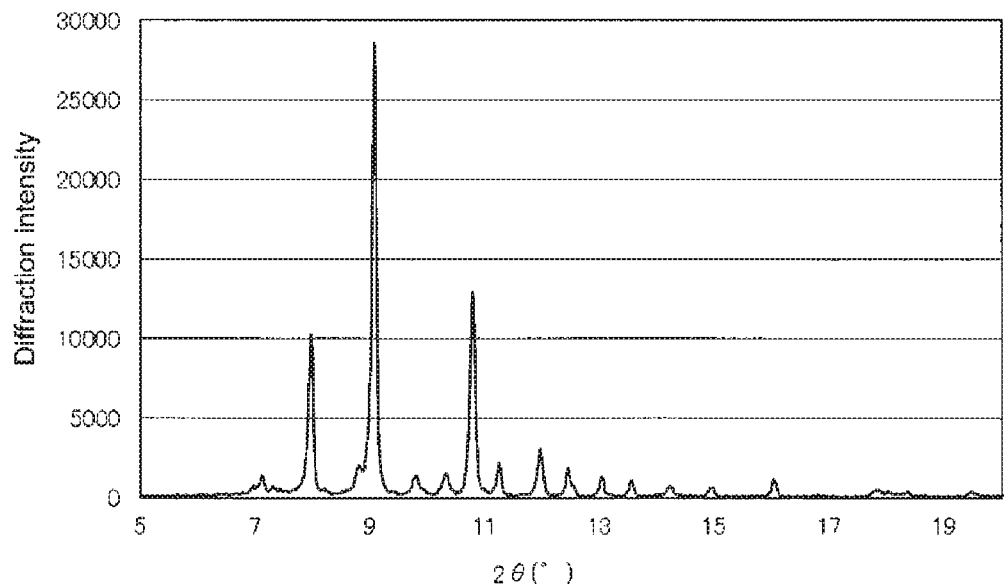
FIG. 5 shows X-ray diffraction spectrum of a preferable complex according to the present invention.
Figure 6:
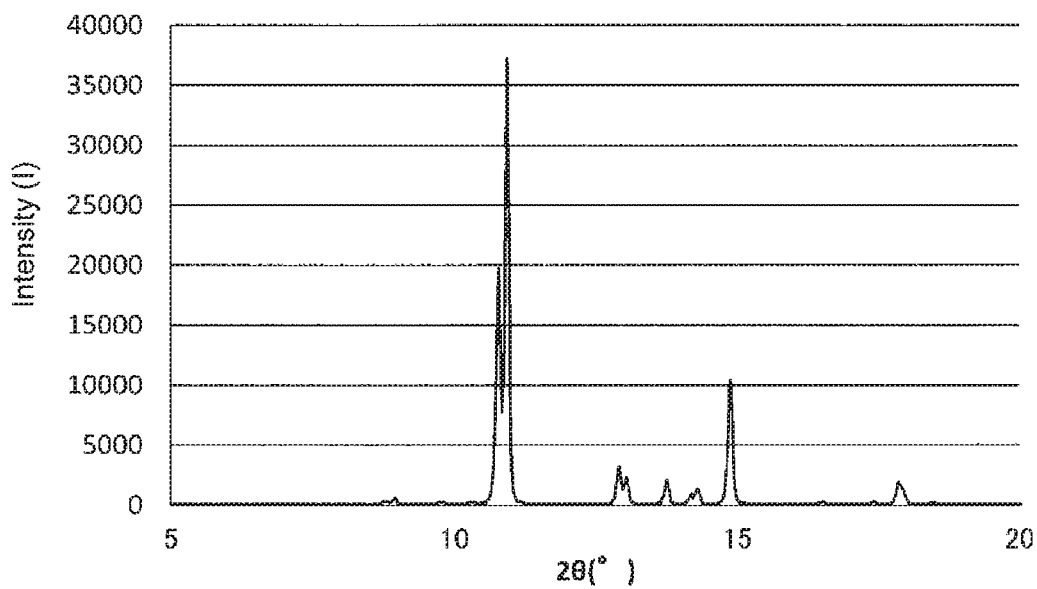
FIG. 6 shows X-ray diffraction spectrum of zinc acrylate.

FIG. 3 shows IR spectrum of the complex according to the present invention, and FIG. 4 shows IR spectrum of zinc diacrylate. FIG. 5 shows X-ray diffraction spectrum of the complex according to the present invention, and FIG. 6 shows X-ray diffraction spectrum of zinc diacrylate. Based on the IR spectra, the absorption attributed to the vinyl group of acrylate and the absorption attributed to the vibration of $Zn_4O$ are confirmed. Further, it is also confirmed that the

TABLE 1

| Inventive preparing example | Compound (3) (g) | (mmol) | Metal oxide (4) (g) | (mmol) | Compound (3)/metal oxide (4) (molar ratio) | Solvent (ml) | Temperature (° C.) | Time (h) | Output (g) | Yield (%) |
|---|---|---|---|---|---|---|---|---|---|---|
| 1 | ZDA 19.1 | 92 | ZnO 2.5 | 31 | 3:1 | Dichloromethane 375 | 40° C. | 3 | 5.54 | 26 |
| 2 | ZDA 955 | 4600 | ZnO 125 | 1540 | 3:1 | Dichloromethane 18700 | 40° C. | 3 | 87.4 | 8 |
| 3 | ZDA 955 | 4600 | ZnO 125 | 1540 | 3:1 | Dichloromethane 18700 | 40° C. | 12 | 306 | 28 |
| 4 | ZDA 955 | 4600 | ZnO 125 | 1540 | 3:1 | Dichloromethane 18700 | 40° C. | 24 | 588 | 54 |
| 5 | ZDA 955 | 4600 | ZnO 125 | 1540 | 3:1 | Dichloromethane 18700 | 40° C. | 48 | 615 | 57 |

ZDA: zinc acrylate

Yield (%) = 100 × (value obtained by dividing each output by molecular weight of cluster)/(theoretical value (mole) of cluster estimated from raw materials)

carboxylate group has a different coordination state from zinc diacrylate. Based on the X-ray diffraction spectra, it is confirmed that the product 5 (zinc acrylate oxo cluster) has a different crystal structure from zinc diacrylate.

Comparative Preparing Example 1

Zinc acrylate (2.0 g, 9.6 mmol) and 140 ml of toluene as a solvent were charged into a reaction vessel to dissolve or disperse zinc acrylate in toluene. Into the reaction liquid, 3 ml of water and 20 mg of 4-methoxyphenol as a polymerization inhibitor were further added as additives. The reaction liquid was stirred for 12 hours while refluxing toluene at 110° C. After finishing the reaction, the reaction liquid was filtered to obtain a filtrate. The filtration residue had a mass of 1.77 g (88.5%). The obtained filtrate was concentrated to obtain a concentrate (0.21 g, 10.5%). The concentrate was analyzed and no target product was confirmed.

Comparative Preparing Example 2

The reaction was conducted by the same method as the comparative preparing example 1 except that chloroform was used as the solvent and the reaction liquid was stirred while refluxing chloroform at 60° C. The filtration residue had a mass of 0.24 g (12%). The obtained filtrate was concentrated to obtain a concentrate (1.44 g, 72%). The concentrate was analyzed and no target product was confirmed.

Comparative Preparing Example 3

The reaction was conducted by the same method as the comparative preparing example 1 except that 140 ml of 1,2-dichlorobenzene was used as the solvent and the reaction liquid was stirred at 110° C. There was no insoluble substance in the reaction liquid. The obtained filtrate failed to be concentrated, and the target product failed to be obtained.

Comparative Preparing Example 4

The reaction was conducted by the same method as the comparative preparing example 1 except that 140 ml of propyl acetate was used as the solvent and the reaction liquid was stirred while refluxing propyl acetate at 100° C. The filtration residue had a mass of 1.71 g (85.5%). The target product failed to be obtained.

Comparative Preparing Example 5

The reaction was conducted by the same method as the comparative preparing example 1 except that 140 ml of acetone was used as the solvent and the reaction liquid was stirred while refluxing acetone at 56° C. The filtration residue had a mass of 0.26 g (13%). The obtained filtrate was concentrated to obtain a concentrate (1.54 g, 77%). The concentrate was analyzed and no target product was confirmed.

Comparative Preparing Example 6

The reaction was conducted by the same method as the comparative preparing example 1 except that 140 ml of N,N-dimethyl formamide (DMF) was used as the solvent and the reaction liquid was stirred at 100° C. There was no insoluble substance in the reaction liquid. The obtained filtrate failed to be concentrated, and the target product failed to be obtained.

Comparative Preparing Example 7

The reaction was conducted by the same method as the comparative preparing example 1 except that 140 ml of acetonitrile was used as the solvent and the reaction liquid was stirred while refluxing acetonitrile at 82° C. There was no insoluble substance in the reaction liquid. The obtained filtrate was concentrated to obtain a concentrate (1.8 g, 90%). The concentrate was analyzed and no target product was confirmed.

Comparative Preparing Example 8

The reaction was carried out by the same method as the comparative preparing example 1 except that 140 ml of dimethylsulfoxide (DMSO) was used as the solvent and the reaction liquid was stirred at 100° C. There was no insoluble substance in the reaction liquid. The obtained filtrate failed to be concentrated, and the target product failed to be obtained.

The preparing conditions and results of the comparative preparing examples 1 to 8 are summarized in Table 2.

TABLE 2

| Comparative preparing example | Raw material | | Additive | | Reaction solvent | | Reaction conditions | | Reaction product | | | | Note |
|---|---|---|---|---|---|---|---|---|---|---|---|---|---|
| | | | Water | 4-Methoxyphenol | Type | ml | Temperature (° C.) | Time (h) | Filtration residue | | Filtrate concentrate | | |
| | g | mmol | | | | | | | (g) | (%) | (g) | (%) | |
| 1 | ZDA 2.0 | 9.6 | 3 ml | 20 mg | Toluene | 140 | Reflux 110° C. | 12 | 1.77 | 88.5 | 0.21 | 10.5 | No target product produced |
| 2 | ZDA 2.0 | 9.6 | 3 ml | 20 mg | Chloroform | 140 | Reflux 60° C. | 12 | 0.24 | 12 | 1.45 | 72 | No target product produced |
| 3 | ZDA 2.0 | 9.6 | 3 ml | 20 mg | 1,2-Dichlorobenzene | 140 | 110° C. | 12 | No insoluble component | | Failed to be concentrated | | No target product produced |
| 4 | ZDA 2.0 | 9.6 | 3 ml | 20 mg | Propyl acetate | 140 | Reflux 100° C. | 12 | 1.71 | 85.5 | — | — | No target product produced |

TABLE 2-continued

| Comparative preparing example | Raw material | | Additive | | Reaction solvent | | Reaction conditions | | Reaction product | | | | Note |
|---|---|---|---|---|---|---|---|---|---|---|---|---|---|
| | | | Water | 4-Methoxyphenol | Type | ml | Temperature (°C.) | Time (h) | Filtration residue (g) | (%) | Filtrate concentrate (g) | (%) | |
| | g | mmol | | | | | | | | | | | |
| 5 | ZDA 2.0 | 9.6 | 3 ml | 20 mg | Acetone | 140 | Reflux 56° C. | 12 | 0.26 | 13.0 | 1.54 | 77 | No target product produced |
| 6 | ZDA 2.0 | 9.6 | 3 ml | 20 mg | DMF | 140 | 100° C. | 12 | No insoluble component | | Solid failed to be obtained | | No target product produced |
| 7 | ZDA 2.0 | 9.6 | 3 ml | 20 mg | Acetonitrile | 140 | Reflux 82° C. | 12 | No insoluble component | | 1.8 | 90 | No target product produced |
| 8 | ZDA 2.0 | 9.6 | 3 ml | 20 mg | DMSO | 140 | 100° C. | 12 | No insoluble component | | Failed to be concentrated | | No target product produced |

ZDA: zinc acrylate
Yield (%) = 100 × (value obtained by dividing each output by molecular weight of cluster)/(theoretical value (mole) of cluster estimated from raw materials)

Comparative Preparing Example 9

Zinc acrylate (5.02 g, 24 mmol) and 200 ml of toluene as a solvent were charged into a reaction vessel to dissolve or disperse zinc acrylate in toluene. Into the reaction liquid, 3 ml of water was further added as an additive. The reaction liquid was stirred for 2 hours while refluxing toluene at 110° C. After finishing the reaction, the reaction liquid was filtered to obtain a filtrate. The obtained filtrate was concentrated to obtain a concentrate (0.38 g, 7.6%). The concentrate was analyzed and no target product was confirmed.

Comparative Preparing Example 10

Zinc acrylate (2.00 g, 9.6 mmol) and 200 ml of toluene as a solvent were charged into a reaction vessel to dissolve or disperse zinc acrylate in toluene. Into the reaction liquid, 2 ml of water was further added as an additive. The reaction liquid was stirred for 2 hours while refluxing toluene at 110° C. After finishing the reaction, the reaction liquid was filtered to obtain a filtrate. The obtained filtrate was concentrated to obtain a concentrate (0.37 g, 18.6%). The concentrate was analyzed and no target product was confirmed.

Comparative Preparing Example 11

Zinc acrylate (2.01 g, 9.7 mmol) and 200 ml of toluene as a solvent were charged into a reaction vessel to dissolve or disperse zinc acrylate in toluene. Into the reaction liquid, 2 ml of water was further added as an additive. The reaction liquid was stirred for 1 hour at 90° C. After finishing the reaction, the reaction liquid was filtered to obtain a filtrate. The obtained filtrate was concentrated to obtain a concentrate (1.07 g, 53.2%). The concentrate was analyzed and no target product was confirmed.

Comparative Preparing Example 12

Zinc acrylate (2.04 g, 9.8 mmol) and 200 ml of toluene as a solvent were charged into a reaction vessel to dissolve or disperse zinc acrylate in toluene. Into the reaction liquid, 0.5 ml of water was further added as an additive. The reaction liquid was stirred for 1 hour while refluxing toluene at 110° C. After finishing the reaction, the reaction liquid was filtered to obtain a filtrate. The obtained filtrate was concentrated to obtain a concentrate (1.67 g, 81.7%). The concentrate was analyzed and no target product was confirmed.

Comparative Preparing Example 13

Zinc acrylate (2.01 g, 9.7 mmol) and 200 ml of toluene as a solvent were charged into a reaction vessel to dissolve or disperse zinc acrylate in toluene. The reaction liquid was stirred for 1 hour while refluxing toluene at 110° C. After finishing the reaction, the reaction liquid was filtered to obtain a filtrate. The obtained filtrate was concentrated to obtain a concentrate (0.30 g, 14.8%). The concentrate was analyzed and no target product was confirmed.

Comparative Preparing Example 14

Zinc acrylate (2.08 g, 10 mmol) and 200 ml of toluene as a solvent were charged into a reaction vessel to dissolve or disperse zinc acrylate in toluene. Into the reaction liquid, 1 ml of water was further added as an additive. The reaction liquid was stirred for 2 hours while refluxing toluene at 110° C. After finishing the reaction, the reaction liquid was filtered to obtain a filtrate. The obtained filtrate was concentrated to obtain a concentrate (0.85 g, 41%). The concentrate was analyzed and no target product was confirmed.

Comparative Preparing Example 15

Zinc acrylate (10 g, 4.8 mmol) and 49 ml of toluene as a solvent were charged into a reaction vessel to dissolve or disperse zinc acrylate in toluene. The reaction liquid was stirred for 5 hours while refluxing toluene at 110° C. After finishing the reaction, the reaction liquid was filtered to obtain a filtrate. The obtained filtrate was concentrated to obtain a concentrate (0.26 g, 2.6%). The concentrate was analyzed and a polymer of zinc acrylate was confirmed.

Comparative Preparing Example 16

Zinc acrylate (10 g, 4.8 mmol) and 49 ml of toluene as a solvent were charged into a reaction vessel to dissolve or disperse zinc acrylate in toluene. The reaction liquid was stirred for 24 hours while refluxing toluene at 110° C. After finishing the reaction, the reaction liquid was filtered to obtain a filtrate. The obtained filtrate was concentrated to obtain a concentrate (0.08 g, 0.8%). The concentrate was analyzed and a polymer of zinc acrylate was confirmed.

Comparative Preparing Example 17

Zinc acrylate (10 g, 4.8 mmol) and 97 ml of toluene as a solvent were charged into a reaction vessel to dissolve or disperse zinc acrylate in toluene. The reaction liquid was stirred for 24 hours while refluxing toluene at 110° C. After finishing the reaction, the reaction liquid was filtered to obtain a filtrate. The obtained filtrate was concentrated to obtain a concentrate (0.03 g, 0.3%). The concentrate was analyzed and a polymer of zinc acrylate was confirmed.

Comparative Preparing Example 18

Zinc acrylate (10 g, 4.8 mmol) and 97 ml of xylene as a solvent were charged into a reaction vessel to dissolve or disperse zinc acrylate in xylene. The reaction liquid was stirred for 5 hours while refluxing xylene at 110° C. After finishing the reaction, the reaction liquid was filtered to obtain a filtrate. The obtained filtrate was concentrated to obtain a concentrate (0.19 g, 1.9%). The concentrate was analyzed and a polymer of zinc acrylate was confirmed.

The reaction conditions and results of the comparative preparing examples 9 to 18 are summarized in Table 3.

TABLE 3

| Comparative preparing example | Material g | mmol | Additive Water | Solvent Type | ml | Reaction conditions Temperature (° C.) | Time (h) | Filtrate concentrate (g) | (%) | Note |
|---|---|---|---|---|---|---|---|---|---|---|
| 9 | ZDA 5.02 | 24 | 3 ml | Toluene | 200 | Reflux 110° C. | 2 | 0.38 | 7.6 | No target product produced |
| 10 | ZDA 2.00 | 9.6 | 2 ml | Toluene | 200 | Reflux 110° C. | 2 | 0.37 | 18.6 | No target product produced |
| 11 | ZDA 2.01 | 9.7 | 2 ml | Toluene | 200 | 90° C. | 1 | 1.07 | 53.2 | No target product produced |
| 12 | ZDA 2.04 | 9.8 | 0.5 ml | Toluene | 200 | Reflux 110° C. | 1 | 1.67 | 81.7 | No target product produced |
| 13 | ZDA 2.01 | 9.7 | 0 | Toluene | 200 | Reflux 110° C. | 1 | 0.30 | 14.8 | No target product produced |
| 14 | ZDA 2.08 | 10.0 | 1 ml | Toluene | 200 | Reflux 110° C. | 1 | 0.85 | 41 | No target product produced |
| 15 | ZDA 10 | 4.8 | 0 | Toluene | 49 | Reflux 110° C. | 5 | 0.26 | 2.6 | Polymer of ZDA |
| 16 | ZDA 10 | 4.8 | 0 | Toluene | 49 | Reflux 110° C. | 24 | 0.08 | 0.8 | Polymer of ZDA |
| 17 | ZDA 10 | 4.8 | 0 | Toluene | 97 | Reflux 110° C. | 24 | 0.03 | 0.3 | Polymer of ZDA |
| 18 | ZDA 10 | 4.8 | 0 | Xylene | 97 | Reflux 110° C. | 5 | 0.19 | 1.9 | Polymer of ZDA |

ZDA: zinc acrylate
Yield (%) = 100 × (value obtained by dividing each output by molecular weight of cluster)/(theoretical value (mole) of cluster estimated from raw materials)

TABLE 4

| Rubber composition | | | 1 | 2 |
|---|---|---|---|---|
| Formulation (parts by mass) | (a) | BR730 | 100 | 100 |
| | (b) | Zinc acrylate oxo cluster | 20 | — |
| | | ZN-DA90S | — | 19.7 |
| | (d) | Zinc oxide | 2.69 | 5 |
| | (c) | Dicumyl peroxide | 0.8 | 0.8 |
| Crosslinking component | | Acrylate (parts by mass) | 12.1 | 12.1 |
| | | Zinc (parts by mass) | 9.6 | 9.6 |
| Evaluation | Molding conditions | Temperature (° C.) | 170 | 170 |
| | | Time (min) | 20 | 20 |
| | Slab properties | Shore C hardness | 60.6 | 62.6 |
| | | Lupke type rebound resilience (%) | 75.0 | 67.2 |

The materials used in Table 4 are shown as follows.

BR730: high-cis polybutadiene (amount of cis-1,4 bond=96 mass %, amount of 1,2-vinyl bond=1.3 mass %, Moony viscosity ($ML_{1+4}$ (100° C.)=55, molecular weight distribution (Mw/Mn)=3) available from JSR Corporation Zinc acrylate oxo cluster: product 5 obtained in the inventive preparing example 5

ZN-DA90S: zinc acrylate (a product coated with zinc stearate in an amount of 10 mass %) available from Nisshoku Techno Fine Chemical Co., Ltd.

Zinc oxide: "Ginrei R" available from Toho Zinc Co., Ltd.

Dicumyl peroxide: "Percumyl (register trademark) D" available from NOF Corporation Table 4 shows the hardness and rebound resilience of the slab formed from the rubber composition. It is apparent that the co-crosslinked rubber molded products (slabs) using the complex according to the present invention each exhibits high resilience performance, thus the usefulness of the complex according to the present invention as a co-crosslinking agent is confirmed.

[Preparation of Rubber Composition]

Materials having the formulations shown in Table 4 were kneaded to prepare rubber compositions. It is noted that the material temperature at the time of kneading the rubber compositions was set as 100° C. to 130° C.

The complex according to the present invention is useful, for example, as a co-crosslinking agent. The at least two carbon-carbon double bonds of the complex can crosslink a compound having an ethylenically unsaturated bond. In particular, the complex according to the present invention is useful as a co-crosslinking agent of a rubber composition, paint composition or adhesive composition. This application is based on Japanese Patent Application No. 2016-250051 filed on Dec. 22, 2016, the content of which is hereby incorporated by reference.

The invention claimed is:

1. A complex of formula (1):

[M$_4$O(RCOO)$_6$]$_n$     (1)

wherein in the formula (1), M is zinc, R is —CH=CH$_2$, and n is an integer of 1 to 8.

2. A complex of structural formula (2):

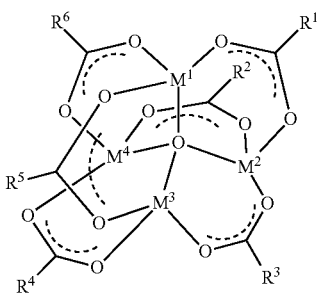

(2)

wherein in the structural formula (2), M$^1$ to M$^4$ are zinc, and R$^1$ to R$^6$ are —CH=CH$_2$.

3. A process for preparing a complex, comprising a step of conducting a reaction between a compound of formula (3) and a metal oxide of formula (4) in a solvent:

[M$^5$(RCOO)$_x$]·yH$_2$O     (3)

M$^6_a$O$_b$     (4)

wherein in the formula (3), M$^5$ is zinc, R is —CH=CH$_2$, x is two, y is zero; and in the formula (4), M$^6$ is zinc, a is one, and b is one, wherein the prepared complex is a complex of formula (1).

4. The process for preparing a complex according to claim 3, wherein dichloromethane is used as the solvent.

5. The process for preparing a complex according to claim 3, wherein a molar ratio ((3)/(4)) of the compound of the formula (3) to the metal oxide of the formula (4) ranges from 3/2 to 5/1.

6. The process for preparing a complex according to claim 3, wherein the reaction is conducted at a temperature in a range from −20° C. to 100° C.

7. The process for preparing a complex according to claim 3, wherein a complex of structural formula (2) is prepared:

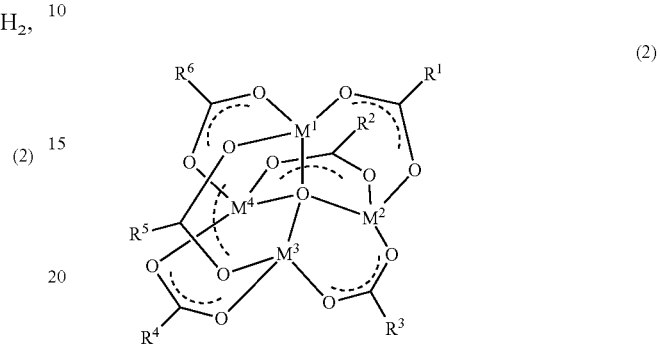

(2)

wherein in the structural formula (2), M$^1$ to M$^4$ are zinc and R$^1$ to R$^6$ are —CH=CH$_2$.

8. The process for preparing a complex according to claim 3, comprising: a step of dissolving or dispersing the compound of the formula (3) and the metal oxide of the formula (4) in a first solvent and stirring the resultant reaction liquid; a step of removing an insoluble substance from the reaction liquid; and a step of removing the solvent from the reaction liquid.

9. The process for preparing a complex according to claim 3, further comprising a step of purifying the obtained complex.

10. The process for preparing a complex according to claim 9, wherein the step of purifying the obtained complex is a step of removing the compound of the formula (3) from the reaction liquid; or a step of performing reprecipitation of a mixture of the complex and the compound of the formula (3) obtained in the preparing process.

* * * * *